United States Patent [19]

Halverson et al.

[11] Patent Number: 4,763,791
[45] Date of Patent: Aug. 16, 1988

[54] DENTAL IMPRESSION SUPPLY KIT

[75] Inventors: George E. Halverson, White Bear Lake; Gerald A. Nelson, New Brighton, both of Minn.

[73] Assignee: Excel Dental Studios, Inc., Minneapolis, Minn.

[21] Appl. No.: 120,240

[22] Filed: Nov. 3, 1987

Related U.S. Application Data

[63] Continuation of Ser. No. 742,221, Jun. 6, 1985, abandoned.

[51] Int. Cl.⁴ .................. B65D 69/00; A61B 19/02
[52] U.S. Cl. .................. 206/570; 206/63.5; 206/369; 206/523; 206/526; 433/37
[58] Field of Search ............ 206/1.7, 1.8, 63.5, 206/368, 369, 372, 370, 363, 83, 570–572, 523, 524, 526, 568; 433/77, 79, 37, 214; 312/DIG. 33; 220/902

[56] References Cited

U.S. PATENT DOCUMENTS

| | | | |
|---|---|---|---|
| 1,123,830 | 1/1915 | Zincke et al. | 433/77 X |
| 1,684,417 | 9/1928 | Silberman | 206/369 X |
| 3,088,584 | 5/1963 | Kozikowski | 206/572 |
| 3,723,061 | 3/1973 | Stahl | 206/370 X |
| 3,777,882 | 12/1973 | McIntyre | 206/523 X |
| 3,802,555 | 4/1974 | Grasty et al. | 206/370 X |
| 3,840,113 | 10/1974 | Bartleson | 206/223 |
| 3,916,527 | 11/1975 | Linkow | 433/37 |
| 3,936,937 | 2/1976 | Gordon | 433/77 |
| 4,153,160 | 5/1979 | Leigh | 206/370 |
| 4,293,074 | 10/1981 | Dunshy | 206/572 |
| 4,294,349 | 10/1981 | Ibsen et al. | 206/63.5 |
| 4,470,488 | 9/1984 | Broussard | 206/1.7 X |
| 4,652,237 | 3/1987 | Cills | 433/37 |

*Primary Examiner*—Stephen Marcus
*Assistant Examiner*—Bryon Gehman
*Attorney, Agent, or Firm*—Burd, Bartz & Gutenkauf

[57] ABSTRACT

A dental impression kit to assist the dentist or a dental technician in the making of dental impressions preparatory to the formation of a mold and the manufacture of a crown or full or partial dentures. The kit contains a compact and orderly arranged array of items necessary or desirable in formation of dental impression. Such items include a selection of upper and lower dental impression trays, dental impression material base and catalyst, adhesive, polish, instructions and a mixing pad. From the kit, the dentist is able to select the appropriate type and size of impression tray, mix the impression base and material on a mixing pad, prepare the tray with the adhesive and then fill it with the impression material and take the dental impression, all the while having instructions at hand if necessary. The finished dentures can be polished using the polish kit. Secondary inventory control cases complement the primary case by making inventory available as items from the primary case are depleted.

11 Claims, 2 Drawing Sheets

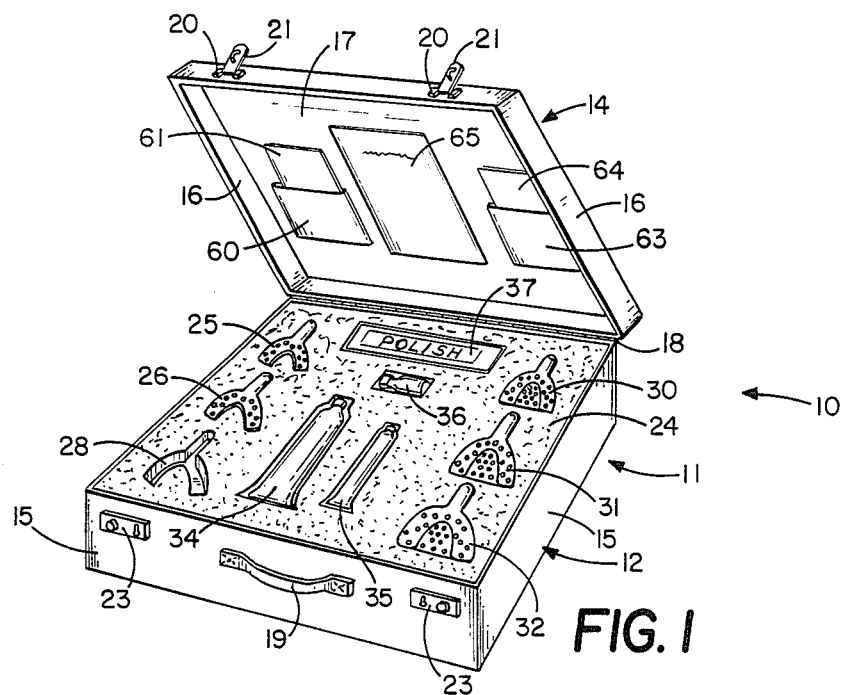
FIG. 1
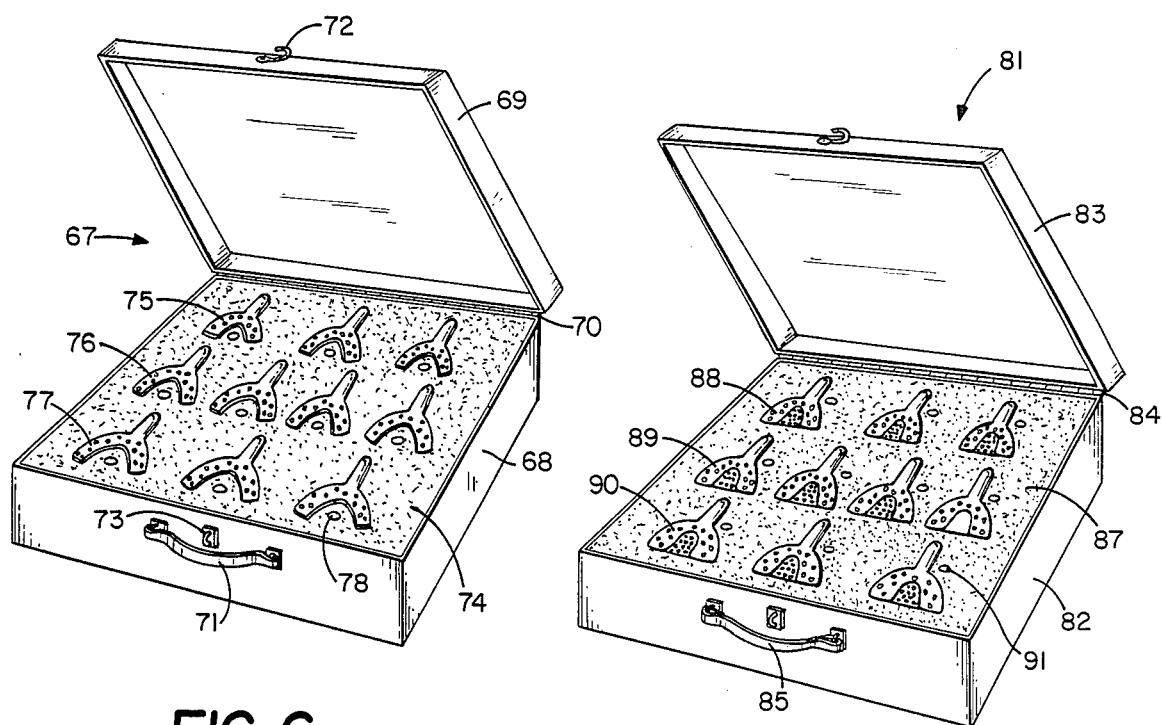
FIG. 6
FIG. 7

DENTAL IMPRESSION SUPPLY KIT

This is a continuation of co-pending application Ser. No. 742,221 filed on June 6, 1985, now abandoned.

BACKGROUND OF THE INVENTION

In the field of human dentistry, the manufacture of fixed crowns, fixed bridges or partial dentures is usually preceded by manufacture of a rigid model corresponding to the affected mouth portion of the patient, i.e., the upper or lower jaw. The model is made from a mold or impression prepared by the dentist or his operative using an impression tray and various other components. For reasons of sanitation and economy, disposable impression trays are used which are available in various sizes for various mouth sizes, as well as upper and lower jaws. The dentist requires a selection of these on hand, as well as other necessary items as impression material base and catalyst, mixing pads and the like. Such items are preferably arranged for purposes of work efficiency and are maintained in inventory so as not to be out of a necessary item at a critical time.

SUMMARY OF THE INVENTION

The invention pertains to a dental impression equipment kit useable by a dentist or technician to prepare an oral impression preparatory to formation of a mold and subsequent manufacture of individual crowns or full or partial dentures. The kit includes a primay case having an ordered assemblage of appropriate components conveniently arranged to enable efficient formation of dental impressions by the dentist or his assistant. The items include a selection of upper and lower impression trays, impression material, adhesive, instructions, mixing pads and the like. An inventory of necessary items is maintained by maintaining secondary cases of the most frequently depleted items such as the dental trays and impression materials. An outside laboratory used by the dentist to manufacture the molds can maintain account of the materials used so as to known when to replenish the inventory from time to time.

IN THE DRAWINGS

FIG. 1 is a perspective view of a dental impression kit according to the invention showing a primary case and containing the various necessary components;

FIG. 6 is a perspective view of a second case of the kit of FIG. 1 comprised as a first inventory control case;

FIG. 7 is a perspective view of a second inventory control case of the kit of FIG. 1.

DESCRIPTION OF A PREFERRED EMBODIMENT

Figure 2:
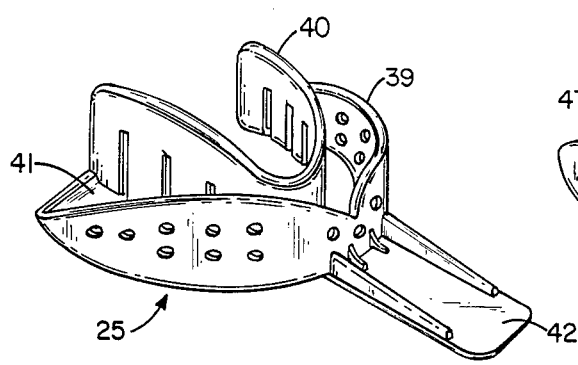
FIG. 2 is an enlarged perspective view of one of the components from the case of FIG. 1 shown to be an impression tray useable with a lower jaw.

Referring to the drawings, there is shown in FIG. 1 a kit 10 according to the present invention including a portable case 11 having an open box-like base 12 and a corresponding cover 14. Case 11 can be decorative to complement the dental office. Base 12 is rectangular in configuration and has perpendicularly orientated upright side walls 15 all connected to a bottom wall (not shown). Cover 14 corresponds in shape and has smaller side walls 16 orientated in perpendicular relationship and connected to a top wall 17. A hinge 18 connects the lower edge of one of the side walls 16 of the cover 14 with an upper edge of one of the side walls 15 of the base 12 for movement of the cover 14 between opened and closed relationship with respect to the base 12 in the usual fashion. A handle 19 is connected to one side wall 15 of base 12 for carrying the case 11 from place to place. Latch means includes a first latch portion 20 having a pivotal latch member 21 located on a wall 16 of the cover 14 opposite that joining the hinge 18. Corresponding latch member receptacles 23 are properly positioned on the wall 15 of base 12 to releasably accept the free ends of the latch members 21 to close the case 11.

Base 12 is filled with a filler material forming a support member 24, such as expanded foam, that is light, rigid and slightly shock absorbent with an accessible upper surface when the cover is open. A plurality of upwardly open compartments or pockets are formed in the upper surface of support member 24 to hold individual items appropriate to the process of making dental impressions. In making a dental impression, an impression tray is filled with formable impression material formed by a mixture of impression material base and catalyst mixed on a sheet from a mixing sheet pad in proportion according to manufacturer's directions. An adhesive can be used to hold the impression material to the impression tray. All such items are readily available in kit 10 and are arranged in orderly fashion for the convenience of the dentist.

Various of these items are stored in kit 10 in base 15 in the pockets which are formed in support member 24 according to the shape of the item. Along one longitudinal edge of base 15, a plurality of lower dental impression trays are stored in close association preparatory to use as needed. Impression trays 25 and 26 are shown in longitudinal alignment with an empty pocket 28 from which a tray has been removed. The pocket 28 is formed generally according to a profile of the missing impression tray. The selection of various trays is provided in order that the dentist can have a selection of sizes of trays to determine the one optimum for the task at hand. Along the opposite longitudinal edge of base 15 is a selection of aligned upper dental impression trays 30, 31, 32 which are of three different sizes, such as small, medium and large, according to the requirements of the dentist. These trays are situated in close association in appropriately shaped pockets so as to be held in place and readily identified. A large tube of impression material base 34 is located intermediate the rows of impression trays and in side-by-side relationship to a smaller tube of impression material catalyst 35. A small bottle of adhesive 36 is located in an appropriately formed pocket just ahead of the tubes of impression material. A denture polishing kit 37 is located ahead of adhesive 36 also in an appropriately formed pocket for use in polishing finished dentures.

Several of the items contained inthe base of kit 10 of FIG. 1 are more fully illustrated in FIG. 2–5. In FIG. 2, a lower dental impression tray 25 is generally U-shaped and has curved outer and inner walls 39, 40 spaced apart a distance to accommodate the lower bite of a patient. Inner and outer walls 39, 40 are connected by an end wall 41. The channel between the walls 39, 40 approximates the lower bite curvature and is filled with the mixed dental impression material which can overflow through the openings shown in the walls when an impression is made by a patient biting down. The trays is formed of relatively inflexible molded plastic. A handle 42 extends centrally from the outer wall 39 to be held by the dentist during the process of forming the impression.

Figure 3:
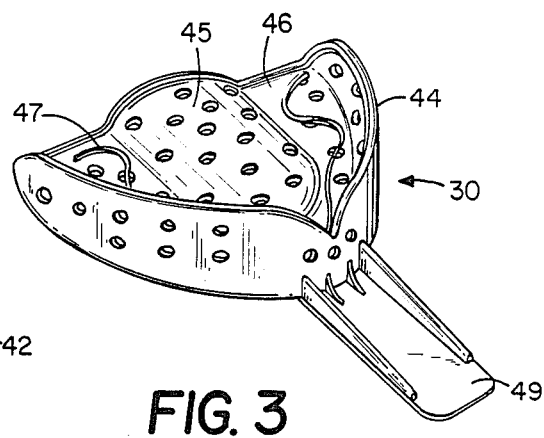
FIG. 3 is a perspective view of another component of the kit of FIG. 1 shown to be an impression tray useable with an upper jaw.

FIG. 3 illustrates an upper dental impression tray 30 having a curved outer wall 44 and a hump portion or curved platform 45 separated by a base or bottom wall 46. The platform 45 generally corresponds in shape to the roof portion of the mouth of a patient, and the curvature of outer wall 44 generally corresponds to the outer curvature of the upper row of teeth. The channel between them holds a portion of mixed impression material and is of a size to accommodate the teeth of the patient when an impression is being made. Suitable openings are provided in the wall 44, platform 45 and end wall 46 for overflow of impression material upon exertion of pressure from the bite of the patient. A ridge 47 trained along the base or end wall 46 is provided as a stop for the patient's teeth. A handle 49 extends forwardly from the central portion of the outer wall 44 to be held by the dentist during the impression forming procedure.

Figure 4:
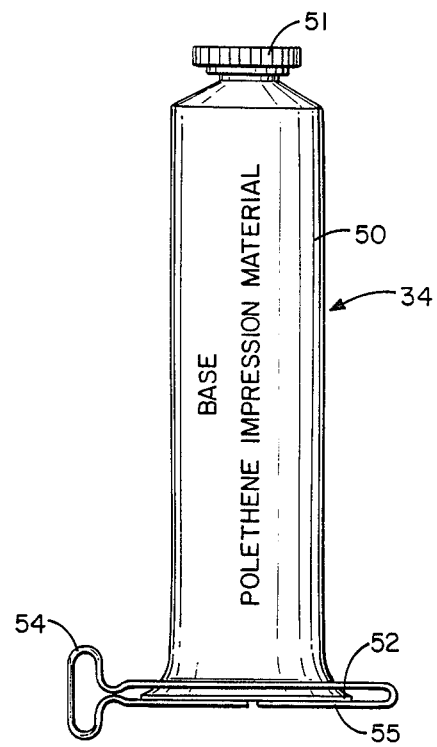
FIG. 4 is a side elevational view of a further component of the kit of FIG. 1 shown as a tube of base impression material.
Figure 5:
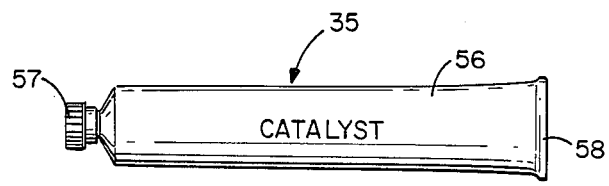
FIG. 5 is a side elevational view of a fourth component of the kit of FIG. 1 shown to be a tube of catalyst impression material.

Referring to FIG. 4, impression base container 34 includes a conventional, generally cylindrical squeeze tube 50 formed of flexible side walls closed at one end by a cap 51 and having a linear lip 52 at the opposite end adapted to be rolled or deformed so as to force material from the open end of the squeeze tube 50 when the cap 51 is removed. To facilitate this movement, a key 54 having an elongate linear loop 55 is adaptable to be trained over the lip 52 and turned so as to rotate the end of the tube, progressively decreasing the volume of the squeeze tube 50 and forcing material out of the open end. As shown in FIG. 5, catalyst container 35 is similar in construction to the base container 34 but somewhat smaller and includes a generally cylindrical somewhat conventional squeeze tube 56 having deformable side walls and an open end closed by end cap 57 at one end. A linear lip 58 at the other end is adapted to be rotated so as to progressively decrease the volume of squeeze tube 56 and force catalyst material out of the open end when the cap 57 is removed.

Referring again to FIG. 1, additional necessary or desirable components or items useable in the impression making procedure are stored with respect to cover 14. A first pouch 60 is secured to the interior surface of top 17 of cover 14 and is upwardly open when the cover is in the open position shown in FIG. 1. Pouch 60 carries a removable card or sheet 61 carrying instruction pertaining to the mixing of the base impression material and the catalyst, and the subsequent steps in forming the impression. A second pouch 63 is also fastened to the interior surface of the top wall 17 of cover 14 toward an edge opposite the first pocket 60 and is upwardly open when the cover is in the open position shown in FIG. 1.

The second pouch 60 advantageously carries a mixing pad 64 which is used in the step of mixing the base with the catalyst of the impression material. Centrally fixed on the interior surface of wall 17 of cover 14 between the first and second pouches 60, 63 is a fixed sheet 65 of instructions pertaining to the use and contents of the kit 10, as well as the subsequent steps to be taken by the dentist or his technician following formation of the dental impression in order to have a finished mold formed. Such instructions can be placed there by a vendor of the kit and materials contained in the kit, such as a dental studio which will subsequently form the mold for the dentist.

Eventually items contained by primary case 11 are depleted and require replacement. For example, for reasons of economy and sanitation, the dental impression trays are preferably disposable after a single use. The impression material and adhesive containers are, of course, depleted through use as well. Accordingly, kit 10 is advantageously complemented by a plurality of secondary cases or inventory control cases to provide an inventory on hand of the more necessary items which are used. As shown in FIG. 6, a first secondary case or inventory control case 67 has an open box-like base 68 formed of perpendicularly orientated side walls, and a complementary cover 69 joined along an edge to the base 68 by a hinge 70. The case can be carried by a handle 71 attached to the bse 68 and the cover and base are closed by cooperating latch parts 72, 73. Case 67 contains an inventory of lower dental impression trays of varying sizes. A support member 74 is provided with rows of pockets to hold the various trays. A first row of lower dental impression trays 75 can be of a small size, and a second row of dental impression trays 76 can be intermediate in size, while a third row of dental impression trays 77 can be large size. Suitable markers or indicia 78 disposed by each tray can indicate the size of the tray and other pertinent information necessary. As a tray of a selected size of the lower dental impression trays from the primary case 11 is used, it is replaced by an appropriate tray from the first inventory control case 67.

In FIG. 7, there is shown a second inventory control case 81 for carrying an inventory of upper dental impression trays. Case 81 includes a base 82 and a corresponding cover 83 connected by a hinge 84. Case 81 can be portably conveyed by a handle 85. Base 82 contains a support member 87 having a plurality of pockets or indentations for accommodating an orderly array of upper denture impression trays including a first row of trays 88 being of a small size, an intermediate row of dental impression trays 89 being of a medium size, and a third row of dental impression trays 90 being of a large size. Tags or labels 91 adjacent the trays can identify the size or other pertinent information pertaining to the tray.

Figure 8:
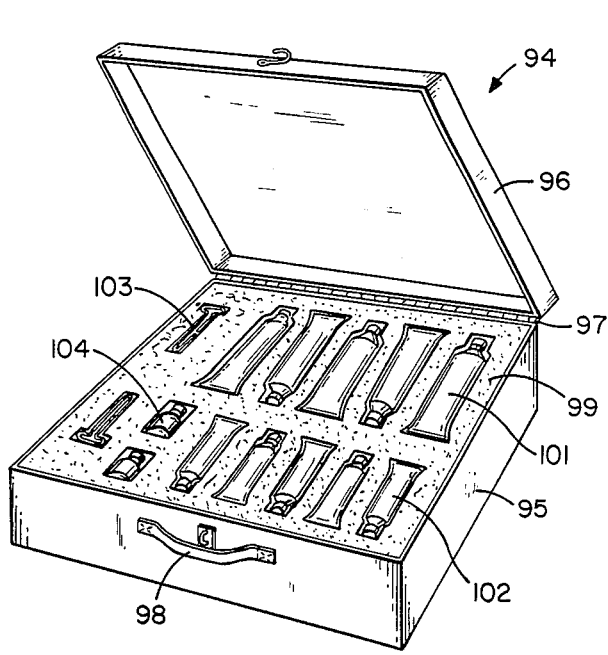
FIG. 8 is a perspective view of a third inventory control case of the kit of FIG. 1.

A third inventory control case 94 is shown in FIG. 8 having an inventory of other necessary or desirable depletable items. Case 94 has a rectangular open top base 95 and a corresponding cover 96 adapted for closure of the base 95 and connected to it by hinge 97, the whole case being portable by a handle 98. A support member 99 in the base 95 has a plurality of orderly arranged pockets of size and shape to particularly accommodate items contained therein. Such items include a first row of tubes 101 of impression material base, and a second row of tubes 102 of impression material catalyst arranged in parallel relationship to the first row of impression material base tubes. Room is provided toward one end of base 95 for pockets to contain a pair of extra wind-up keys 103 used in dispensing material from the base and catalyst tubes. Also, a pair of pockets provide room to hold a pair of bottles 104 of adhesive.

The dental office can operate in cooperative relationship with a dental studio, whereby the studio also is the supplier of materials to the dental office. As the studio receives the impression-laden trays from the dental office for the formation of molds, it records the number and size of trays and is able to determine the depletion of inventory from the dental office, as well as estimate the amount of impression material and other items being used. Accordingly, it can periodically replenish these items in the dental office so that the dental office will be assured that there is adequate stock on hand without having itself to take inventory and notify the dental studio.

While there has been shown and described a preferred embodiment of a dental impression kit according to the invention, it will be apparent that certain alterations can be had therefrom without departing from the scope and spirit of the invention.

The embodiments of the invention in which an exclusive property or privilege is claimed are defined as follows:

1. A dental impression supply kit comprising:
   a primary case having a base and a cover, said cover movable into and out of covering relationship to the base;
   a support member located in and substantially filling the base and having an accessible upper surface when the cover is in position out of covering relationship to the base;
   a first plurality of items appropriate to procedures for forming dental impressions;
   said support member having a corresponding plurality of upwardly open pockets for holding said first plurality of items, each pocket being individually shaped generally in conformance with the shape of an item to be held;
   said first plurality of items including one each of a small size, a medium size, and large size disposable upper dental impression trays;
   said pockets including a first row of three pockets having a first shape in conformance with the shape of an upper dental impression tray;
   said upper dentral impression trays being located in said first row of pockets;
   a first secondary case having a base and a cover movable into and out of covering relationship to the base, a support member located in and substantially filling the base, a plurality of upwardly open pockets having said first shape located in the support member, a plurality of disposable upper dental impression trays of small, medium and large sizes located in said pockets for replenishment of upper dental impression trays depleted from the primary case;
   said first plurality of items also including one each of a small size, a medium size and large size lower disposable dental impression trays;
   said pockets including a second row of three pockets having a second shape in conformance with the shape of a lower dental impression tray;
   said lower dental impression trays being located in said second row of pockets;
   a second secondary case having a base and a cover movable into and out of covering relationship to the base, a support member located in and substantially filling the base, a plurality of upwardly open pockets having said second shape located in the support member, a plurality of disposable lower dental impression trays of small, medium and large sizes located in said pockets for replacement of lower dental impression trays from the primary case;
   others of said items being located in corresponding pockets of the support member of the primary case and including a depletable container of impression material base, a depletable container of impression material catalyst, and a depletable container of adhesive material for forming a dental impression using one of the upper dental impression trays and one of the lower dental impression trays from the primary case.

2. The dental impression kit of claim 1 wherein: said primary case cover is hingedly connected to the primary case base and has an interior surface carrying holding means for holding a second plurality of items appropriate to dental impression procedures, said second plurality of items including an instruction sheet and a mixing pad.

3. The dental impression kit of claim 2 including: a second instruction sheet fixed to the inner surface of the cover providing directions for use of the dental kit.

4. The dental empressions kit of claim 3 wherein: said first plurality of items includes a dental polish kit.

5. The dental impression kit of claim 1 including: a third secondary case, said third secondary case carrying a plurality of replacement containers of dental impression base, a plurality of replacement containers of dental impression catalyst, and at least one replacement container of adhesive for replacement of corresponding items from the primary case.

6. The dental impression kit of claim 5 wherein: said lower impression dental trays are the type having a generally V-shape with an interior wall spaced from an exterior wall by a bottom wall forming a channel for filling with impression material, and a handle extended from the exterior wall.

7. The dental impression kit of claim 6 wherein: said upper impression trays are of the type having an outer wall, a curved inner platform corresponding to the roof of a mouth, and a bottom wall connecting the curved platform and the outer wall forming a channel to be filled with dental impression material, said channel being generally shaped according to the upper dentures of a person, and a handle extended forwardly from the outer wall.

8. The dental impression kit of claim 7 wherein: said base of the primary case is comprised as a box-like housing with an open top, said first selection of dental impression trays comprising first, second and third trays of small, medium and large size arranged in a row proximate one edge of said base, said second selection of dental impression trays comprising first, second and third dental trays of small, medium and large size arranged proximate an opposite edge of said base, said remainder of the first plurality of items being located between the first and second selections of dental trays.

9. The dental impression kit of claim 8 including: latch means to latch the cover with respect to the base when in covering relationship to the base.

10. A dental impression supply kit comprising:

a primary case having a generally rectangular upwardly open base with perpendicularly orientated side walls and a bottom wall connected to the side walls;

a cover for said base having perpendicularly orientated side walls generally corresponding in shape to the side walls of the base, and a top wall connected to the side walls, said cover having a first side wall hingedly connected to a first side wall of the base for movement between positions in and out of covering relationship to the base;

a first plurality of items appropriate to procedures for forming dental impressions;

support means in the base having a corresponding plurality of upwardly open pockets for holding said first plurality of items, each pocket being individually shaped genreally in conformance with the shape of an item to be held;

said plurality of open pockets including a first row of three pockets proximate an edge of a second side wall of a box perpendicular to the first side wall, said pockets each having the shape of a lower dental impression tray, and a second row of three pockets disposed proximate an edge of a third side wall of the box perpendicular to the first side wall and having the shape of an upper dental impression tray;

said items including small, medium and large disposable lower dental impression trays located in said first row of pockets, small, medium and large disposable upper dental impression trays located in said second row of pockets, a depletable container of impression material base and a depletable container of impression material catalyst usable with an upper dental impression tray and a lower dental impression tray to form a dental impression, and a container of adhesive material located between the rows of dental impression mold trays;

first and second pouches located on the interior surface of the cover for holding a second plurality of items, said second plurality of items including a sheet of instructions and a mixing pad;

a first secondary case having a base and a cover movable into and out of covering relationship to the base, a support member located in and substantially filling the base, a plurality of upwardly open pockets having the shape of an upper dental impression tray located in the support member, a plurality of disposable upper dental impression trays of small, medium and large sizes located in said pockets of the first secondary case for replenishment of upper dental impression trays depleted from the primary case;

a second secondary case having a base and a cover movable into and out of covering relationship to the base, a support member located in and substantially filling the base, a plurality of upwardly open pockets having the shape of a lower dental impression tray located in the support member, a plurality of disposable lower dental impression trays of small, medium and large sizes located in said pockets of the second secondary case for replenishment of lower dental impression trays depleted from the primary case.

11. The dental impression kit of claim 10 including: a third secondary case, said third secondary case carrying a plurality of replacement containers of dental impression base, a plurality of replacement containers of dental impression catalyst, and at least one replacement container of adhesive for replacement of corresponding items from the primary case.

* * * * *